United States Patent [19]
Geier et al.

[11] Patent Number: 6,020,374
[45] Date of Patent: Feb. 1, 2000

[54] BIOLOGICALLY ACTIVE SYNTHETIC DYE COMPOUNDS

[75] Inventors: Avraham Geier, Raanana; Hannah Kanety, Givataim; Avraham Karasik, Tel-Aviv, all of Israel

[73] Assignee: Ramot University Authority for Applied Research & Industrial Development Ltd., Ramat-Aviv, Israel

[21] Appl. No.: 09/078,495

[22] Filed: May 14, 1998

[51] Int. Cl.$^7$ .......................... A61K 31/185; A61K 31/19
[52] U.S. Cl. .......................... 514/553; 514/568; 514/638; 514/641
[58] Field of Search .................................. 514/638, 641, 514/553, 568

[56] References Cited

U.S. PATENT DOCUMENTS 5,428,163   6/1995   Mills ........................................ 544/232

FOREIGN PATENT DOCUMENTS 9103226   3/1991   WIPO .

OTHER PUBLICATIONS

Geier, A., et al., "Multiple Pathways are Involved in Protection of MCF–7 Cells Against Death Due to Protein Synthesis Inhibition," *Journal of Cellular Physiology* 163:570–576 (1995).

Benezra, M., et al., "Reversal of Basic Fibroblast Growth Factor–mediated Autocrine Cell Transformation by Aromatic Anionic Compounds," *Cancer Research* 52:5656–5662 (1992).

Mias, H–Q., et al., "Modulation of Fibroblast Growth Factor–2 Receptor Binding, Dimerization, Signaling, and Angiogenic Activity by a Synthetic Heparin–mimicking Polyanionic Compound," *The American Society for Clinical Investigation, Inc.* 99–7:1565–1575 (1997).

Benezra, M., et al., "Antiproliferative Activity to Vascular Smooth Muscle Cells and Receptor Binding of Heparin–Mimicking Polyaromatic Anionic Compounds," *Arteriosclerosis and Thrombosis* 14–12:1992–1999 (1994).

Regan, J.R., et al., "Mimicry of Biological Macromolecules of Polyaromatic Anionic Compounds," *Journal of Bioactive and Compatible Polymers* 8:317–337 (1993).

Cushman, M., et al., "Synthesis and Anti–HIV Activities of Low Molecular Weight Aurintricarboxylic Acid Fragments and Related Compounds," *J. Med. Chem* 34:337–342 (1991).

Whittaker et al. British Journal of Obstetrics and Gynaecology, 100 (6) 587–92 U.K. (Abstract), 1993.

*Primary Examiner*—Theodore J. Criares
*Attorney, Agent, or Firm*—Browdy and Neimark

[57] ABSTRACT

A pharmaceutical composition comprising, in admixture with a pharmaceutically acceptable carrier, a therapeutically effective amount of a polyaromatic ring-containing compound, capable of mimicking the physiological activity of insulin or insulin-like growth factor.

16 Claims, 17 Drawing Sheets

BIOLOGICALLY ACTIVE SYNTHETIC DYE COMPOUNDS

FIELD OF THE INVENTION

The present invention is in the field of biologically active compounds and more specifically to compounds possessing insulin-like activity or insulin-like growth factor-like activity.

BACKGROUND OF THE INVENTION

The hormone insulin stimulates the uptake of glucose into its target cells by binding to a specific receptor on the cell surface. The insulin receptor (IR) is a so-called receptor tyrosine kinase. Binding of insulin to IR causes the receptor to autophosphorylate tyrosine residues present in its catalytic domains. This activated receptor phosphorylates proteins known as insulin receptor substrates (IRS) on multiple tyrosines. The phosphotyrosines on IRS-1 and -2 then serve as high affinity binding sites for the docking and activation of other intracellular signaling proteins including phosphatidyl-inositol-3'-kinase (PI3-kinase).

The hormone insulin-like growth factor I (IGF-1) is known to have a broad range of effects including promotion of cell survival, stimulation of metabolism, and proliferation of differentiating cells. The receptor to this hormone (IGFR) is also a receptor tyrosine kinase whose activation by IGF-I binding leads to phosphorylation of IRS proteins, and their association with and activation of PI3-kinase, the guanine nucleotide exchange factor Grb2/SOS and mitogen activated protein kinases (MAPKs).

Diabetes mellitus is a condition characterized by hyperglycemia due to a deficiency or reduced effectiveness of insulin, impaired access of insulin to its receptor, inactivation of insulin by antibodies, or receptor defects. Treatment of diabetes in cases of insulin deficiency or severe resistance is by administration of exogenous insulin. However, apart from being expensive, insulin treatment is inconvenient as the exogenous insulin must be injected into the patient. It would be desirable to have a substance capable of bypassing the resistance factor and mimicking the effects of insulin and that could be administered orally.

Several negatively charged polyaromatic compounds that mimic many of the physiological effects of heparin have been identified. These compounds, among which are commercially available synthetic dyes, compete with heparin for binding onto cell surfaces. These compounds have been shown to cause reversal of basic fibroblast growth factor-mediated autocrine cell transformation[2], modulation of fibroblast growth factor binding to its receptor, angiogenic activity[3], and antiproliferative activity in vascular smooth muscle cells.[4,5]

International Application in the name of Wher International Holdings discloses anionic polyaromatic compounds that mimic pharmacological activities of glycosaminoglycans. These compounds alter the tissue distribution of biologically active peptides and proteins normally bound to glycosaminoglycans. The compounds are used as anticoagulants, and in the treatment of cardiovascular and neurological disorders.

An example of such an anionic polyaromatic compound is aurintricarboxylic acid (ATA). ATA is capable of forming polymers of variable molecular weight and is known to exhibit a variety of biological activities including inhibition of nucleic acid binding enzymes, platelet aggregation, cytopathogenic effects of HIV-1, and the binding of interferon to its receptor. It is also known to bind to the polynucleotide domains of glucocorticoid receptors and di-hydroxy vitamin D receptors. ATA has been known to protect cells from apoptosis induced by growth factor deprivation or by drugs such as cycloheximide (CX)[1]. It has also been shown to increase tyrosine phosphorylation of several proteins in PC12 cells including Shc, PI3-kinase and MAPKs. It has also been shown to induce tyrosine phosphorylation of erbB4 (a member of the epidermal growth factor receptor family).

EB, is an aromatic polysulfated anion that inhibits various DNA polymerases and endonucleases. It has also been shown to inhibit HIV-mediated cytopathogenicity and to enhance the survival of renal tubular epithelial cells exposed to $H_2O_2$, and breast cancer cells exposed to CX. EB is known to be non-toxic to humans at high doses.

SUMMARY OF THE INVENTION

The present invention relates to pharmaceutical compositions capable of mimicking the physiological activity of insulin or insulin-like growth factor comprising a pharmaceutically acceptable carrier and as active ingredient a therapeutically effective amount of a polyaromatic ring-containing compound capable of mimicking the physiological activity of insulin or insulin-like growth factor.

This invention also relates to therapeutic methods for the treatment of disorders involving insulin or insulin-like growth factor comprising the administration to a subject in need of such treatment an effective amount of a polyaromatic ring-containing anionic compound.

The present invention further concerns use of polyaromatic ring-containing compounds for the preparation of a medicament for the treatment of disorders involving insulin or insulin-like growth factor.

The term "disorders involving insulin or insulin-like growth factors" refers to disorders caused by insufficient amount of insulin or insulin-like growth factor, such as diabetes, growth defects, states where the body cannot supply the optimal amount of IGF-1 or where IGF-1 has an added anti-catabolic or anabolic effect (i.e. burns, sepsis, post-surgical states, cardiomyopathy, aging, osteoporosis, neurodegenerative diseases). Also included are disorders in which the subject, although having a normal amount of insulin, or insulin-like growth factor, nevertheless does not respond normally to these hormones due to impaired receptors to either of these hormones, or desensitization to these hormones.

As employed above and throughout the disclosure, the following terms, unless otherwise indicated, shall be understood to have the following meanings:

Alkyl—means a saturated alipathic hydrocarbon which may be either straight or branched chain containing from about 1 to about 12 carbon atoms.

Lower alkyl—means an alkyl group as above, having 1 to about 4 carbon atoms.

Substituted phenyl—means a phenyl group substituted with one or more substituents which may be alkyl, alkoxy, amino, nitro, carboxy, carboalkoxy, cyano, alkyl amino, halo, hydroxy, hydroxyalkyl, mercaptyl, alkyl mercaptyl, carboalkyl or carbamoyl.

The polyaromatic ring-containing compounds may be monomers preferably containing one to ten aromatic rings, and having a molecular weight of about between 200 and 2,000 Daltons. The aromatic rings may be fused or unfused. Polymers of these compounds are also included within the scope of the invention. Such polymers may be homopolymers or heteropolymers. The polymers may be linear or branched and preferably have a molecular weight of about 1,000 to about 30,000.

Preferred pharmaceutical compositions include compounds having, on at least two of the aromatic rings, one or more substituents selected from the group consisting of $NRR_1$, —N=R, —OR, =O, —$NO_2$, —COOR, halogen, —$SO_2OR$, —$SO_2NHR$, —$OSO_2OR$ and R, wherein R is C1–C12 alkyl or hydrogen and $R_1$ is lower alkyl, hydrogen, phenyl or substituted phenyl.

Examples of such polyaromatic ring-containing compounds as well as a specification of their manner of production and preparation may be found in references 2–7 present in the list of references.

Exemplary compounds known per se, and therefore within the scope of the present invention include Aurintricarboxylic acid (ATA), Evan's Blue (EB), Halogenated ATA, Sulfonated ATA, Sulfonated-Halogenated ATA, phosphorylated ATA, Anazolene Sodium, Eosine I Bluish, Eosine Yellowish, Erythrosine, Fast Green FCF, Fuchin(e) Acid, Iodophthalein Sodium, Rose Bengal, Sulfobromophthalein Sodium, Suramin Sodium, Trypan Blue, Trypan Red, Rosaniline Chloride, Crystal Violet, Methyl Blue, Methyl Green, Coomassie Blue, Basic Fuchsin, Malachite Green, Brilliant Green, Aniline blue, Brilliant Cresyl Blue, Safranin O, Ethyl Violet, Pararosaniline Acetate, Methyl Violet, Direct Yellow, Direct Red, Ponceau S, Ponceau SS, Nitrosulfonazo III, Chicago Sky Blues, calcion and RG-13577, heparin, heparin sulfate poly(9-vinyladenine), poly(1-vinyluracil), pyran co-polymer, chloramphenicol ester of maleic acid and 10-undecendyl copolymer, poly-N-oxides, copolymer with formaldehyde and polyacrylamide sialic acid copolymer].

Such compounds are known to be useful as color additives, diagnostic aids, antiseptic agents or to treat infectious disease. However, none of these compounds has previously been described as useful as or used as a substitute for insulin or insulin-like growth factor.

The anionic polyaromatic ring-containing compounds of the method or composition of the invention may exist in enolic or tautomeric forms, and all of these forms are considered to be included within the scope of this invention.

The compounds included in the compositions of this invention may be useful in the form of the free base, in the form of salts, esters and as hydrates. All fonns are within the scope of the invention. Acid addition salts may be formed and are simply a more convenient form for use and in practice, use of the salt form inherently amounts to use of the base form. The acids that can be used to prepare the acid addition salts include preferably those which produce, when combined with the free base, pharmaceutically acceptable salts, i.e., salts whose anions are non-toxic to the animal organism in pharmaceutical doses of the salts, so that the beneficial pharmacological properties inherent in the free base are not vitiated by any side effects attributable to the anions. Although pharmaceutically acceptable salts of the basic compound are preferred, all acid addition salts are useful as sources of the free base form even if the particular salt per se is desired only as an intermediate product as, for example, when the salt is formed only for purposes of purification and identification, or when it is used as an intermediate in preparing a pharmaceutically acceptable salt by ion exchange procedures. Pharmaceutically acceptable salts of the compounds useful in the practice of this invention are those derived from the following acids: mineral acids such as hydrochloric acid, sulfuric acid, phosphoric acid and sulfamic acid; and organic acids such as acetic acid, citric acid, lactic acid, tartaric acid, malonic acid, methane-sulfonic acid, ethanesulfonic acid, benzenesulfonic acid, p-toluene-sulfonic acid cyclohexylsulfamate and quinate, respectively.

Without wishing to be bound by a particular theory, these compounds may bind to an extracellular domain of IR or IGFR, causing the tyrosine receptor kinase complex to adopt a conformation favoring autophosphorylation of the receptor kinase domain. It is believed that phosphorylation within the kinase domain, significantly increases catalytic activity, leading to increased tyrosine phosphorylation of cellular substrates and to the metabolic effects associated with insulin or IGF-1. These compounds are thus the first known non-peptidic agonists for IR and IGFR.

The man versed in the art, will no doubt be aware that the polyaromatic ring-containing anionic compounds of the invention include a very large number of compounds, some of which are more active than the others. In order to screen for the most active compounds, the following assays should be employed:

i. Compounds which cause tyrosine phosphorylation as specified in Example 1 in the detailed description of the invention;

ii. Tyrosine phosphorylation of IRS-1 and IRS-2 as specified in Example 2;

iii. Stimulation of tyrosine phosphorylation by IGF-1 receptor as specified in Example 3;

iv. Activation of MAPKs as specified in Example 4;

v. Phosphorylation of IR by the compounds as specified in Example 6 and 8;

vi. Phosphorylation of IRS-1 and IRS-2 and their association with PI3-kinase as exemplified in Example 7;

vii. Increase of glucose uptake, glycogen synthesis and lipogenesis as determined in Example 9;

viii. Cell survival enhancing activity as determined in Example 10.

Compounds which cause an insulin or insulin-like growth factor, effect in at least one of the above assays, are preferred compounds in accordance with the invention.

DESCRIPTION OF THE DRAWINGS

The invention will now be described by way of example only, with reference to the accompanying drawings, in which.

Figure 1:
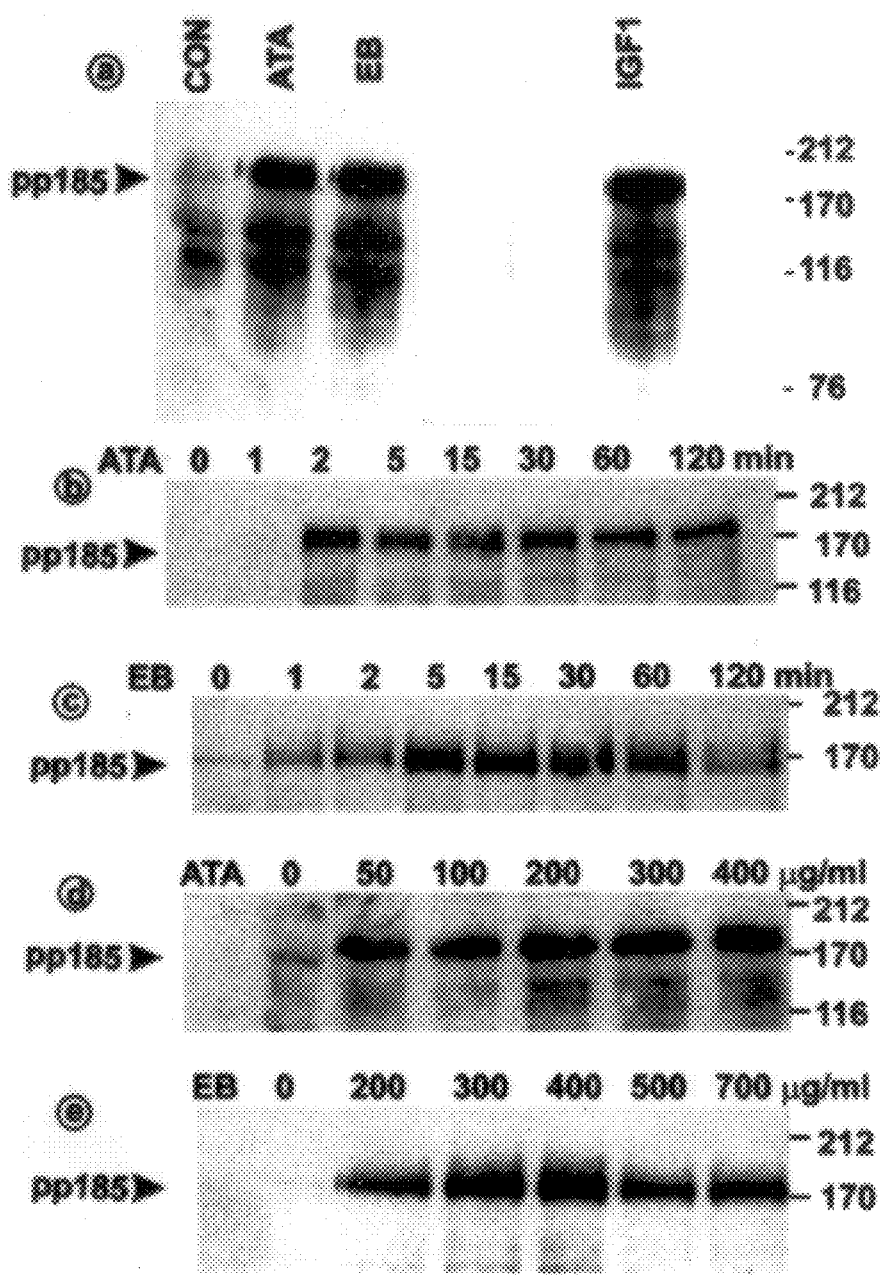
FIG. 1 is the effect of ATA and EB on tyrosine phosphorylation: MCF-7 cells, grown in 35 mm dishes were solubilized in Buffer A (a) or Buffer B (b–c). The solubilized cells were subjected to 7.5% SDS-PAGE and immunoblotted with an anti-phosphotyrosine antibody. (a) Cells treated for 5 mins. with ATA, EB, each at 300 µg/ml, IGF-1 at 20 ng/ml, or without additives (CON); (b) Cells treated with 300 µg/ml ATA for the indicated times; (c) Cells treated with 30 µg/ml EB for the indicated times; (d) Cells treated for 5 mins. with the indicated concentrations of ATA; (e) Cells treated for 5 mins. with the indicated concentrations of EB. Molecular mass markers (in kDa) are indicated on the right.

B—Kinetics of IR phosphorylation: Cells were treated either with 200 μg/ml EB for the indicated times (top panel) or with the indicated concentrations of EB for 5 mins. (middle panel). A 3 hour preincubation with vanadate preceded the 5 min. incubations with EB and insulin (bottom panel).

C—Induction of PI3-kinase: Cells were treated as described in the legend to FIG. 9A. PI3-kinase bound to IRS-1 was immunoprecipitated from the cells with antibody to IRS-1 and assayed for activity. The immunoprecipitates were incubated with phosphatidylinositol and $\gamma^{32}$P-ATP for 10 mins. Lipids were extrated and analyzed by thin-layer chromatography (TLC) on silica gel TLC plates using a chloroform/methanol/ammonium hydroxide (90:70:20 V/V) running buffer. An autoradiogram of the TLC plate is shown. Arrows indicate the position of radioactivity corresponding PI3-monophosphate (PIP) and the origin. The results are representative of 3 to 5 independent experiments.

FIG. 10 is the tyrosine phosphorylation of the IR cascade in rat liver extracts:

A—Immunoblot analysis. Rat liver extracts were subjected to immunoprecipitation and blotting with the indicated antibodies, as described in the legend to FIG. 9A.

B—Induction of PI3-kinase. PI3-kinase activity, 5 mins. after injection was assayed as described in FIG. 9C. The results are representative of 2 to 4 independent experiments.

FIG. 11 is the metabolic effects in 3T3 L1 adipocytes: Fully differentiated 3T3 L1 adipocytes were incubated with EB, ATA or fuchsin (FUCH) each at 200 μg/ml, or with 600 ng/ml of insulin for 20 mins. (A, B, C) or 5 mins. (D). CON indicates no additive.

A—2-deoxyglucose uptake. Hexose uptake was measured for 10 mins. using 50 μM 2-deoxy-($^3$H) glucose (1 μCi/ml). Non-specific uptake was determined in the presence of cytochalasin B (50 μM).

B—Glycogen synthesis. Cells were incubated with ($^{14}$C)-glucose for 10 mins. Radioactivity was determined in the precipitated glycogen fraction.

C—Lipogenesis. Cells were incubated with 5 mM(U-$^{14}$C) glucose (1 μCi/ml) for 60 mins. Radioactivity was determined in the cellular lipid fraction.

D—Protein-tyrosine phosphorylation analysis. Total cell extracts and immunoprecipitates of the 3T3 L1 cell extracts were analyzed by immunoblotting with the indicated antibodies as described in the legend to FIG. 9A. The results are representative of 3–4 independent experiments.

EXAMPLES

1. Experimental Procedures

Materials

Recombinant human IGF-1 was obtained from Boehringer Mannheim (Germany). Protein G0 and protein A-Sepharose were from Pharmacia Biotech, Inc. All other chemicals were from Sigma.

Antibodies

Monoclonal anti-phosphotyrosine antibody (PY-20) was from Transduction Laboratories (Lexington, Ky.). IRS-1 immuno-precipitation was performed with a rabbit polyclonal antibody raised against a synthetic peptide corresponding to the carboxyl-terminal 14 amino acid of rat IRS-1. IRS-1 immunoblotting was performed with a polyclonal antibody from Upstate Biotechnology, Inc. (Lake Placid, N.Y.). Polyclonal anti-IRS-2 antibody and polyclonal anti-p85 (PI3-kinase) antibody were from Upstate Biotechnology, Inc. (Lake Placid, N.Y.). Polyclonal anti-active MAPK antibody was from Promega Corporation (Madison, Wis.), monoclonal anti-MAPK (ERK 1+2) antibody was from Zymed (San Francisco, Calif.). Polyclonal anti-Grb2 antibody was from Santa Cruz Biotechnology, Inc. (Santa Cruz, Calif.). Immuno-precipitation of IGFR was performed with an anti-IGFR antibody from Oncogene Science, Inc. (Uniondale, N.Y.), and IGFR immunoblotting was performed with a polyclonal antio-IGFR β subunit antibody from Santa Cruz Biotechnology, Inc. Immunoprecipitation and immunoblotting of IR is performed with an anti-IR antibody from Transduction Laboratories.

Cell Culture

MCF-7 cells were grown in 35 or 100 mm dishes in DMEM with 5% bovine fetal serum. Rat hepato FaO cells were grown in RPMI 1640 medium supplemented with 10% fetal calf serum. Subconfluent monolayers of MCF-7 cells or FaO cells, were deprived of serum for 20 hours prior to each experiment. The medium was removed, and cells were incubated at 37° C. under the conditions as indicated for each experiment. The reaction was terminated by removing the medium and freezing the monolayers with liquid nitrogen. In some experiments, cells were preincubated with 50 $\mu$M sodium orthovanadate for 3 hours.

Buffers

Buffer A: 50 mM HEPES, pH 7.6, 150 mM sodium orthovanadate, 80 mM β-glycerophosphate, 10 mM NaF, 10 mM sodium pyrophosphate, 2 mM sodium EGTA, 2 mM sodium EDTA, 1% Triton X-100 and 0.1% SDS.

Buffer B: 25 mM Tris-HCl, pH 7.4, 3 mM sodium orthovanadate, 0.5 mM sodium EGTA, 10 mM NaF, 10 mM sodium pyrophosphate, 80 mM β-glycerophosphate, 25 mM NaCl, and 10 mM $MgCl_2$.

Buffer C: 50 mM Tris-HCl, pH 7.4, 1% NP-40, 0.25% sodium deoxycholate, 150 mM NaCl, 1 mM sodium EGTA, 1 mM sodium orthovanadte, 1 mM NaF.

Buffer D: 100 $\mu$M sodium orthovanadate and 1% NP-40 in 1×PBS).

Buffer E: 100 mM Tris-HCL, pH 7.5, 500 mM LiCl, and 100 $\mu$M sodium orthovanadte.

Buffer F: 100 mM Tris-HCL, pH 7.5, 100 mM NaCl, 1 mM EDTA and 100 $\mu$M sodium orthovanadate.

All the buffers contained 1 mM phenylmethylsulfonyl fluoride, 10 $\mu$g/ml leupeptin, and 10 $\mu$g/ml trypsin inhibitor.

SDS-PAGE

Cells were solubilized at 4° C. with 0.2 ml/35 mm dish or 2 ml/100 mm dish of the indicated buffer. The solubilized cells were scraped and sedimented by centrifugation at 12,000×g for 30 mins. at 4° C. Aliquots of the supernatants were normalized for protein, mixed with concentrated (5×) Laemmli sample buffer, boiled for 10 mins. and resolved on 7.5 or 12% SDS-PAGE under reducing conditions.

Immunoprecipitation

Cells were solubilized in Buffer A or C. Extracts were immunoprecipitated at 4° C. with antibodies to IRS-1, IRS-2, IGF-1 or IR receptor or Grb2, adsorbed on protein A-Sepharose beads. The immunocomplexes were pelleted by centrifugation at 12,000×g and washed twice with Buffer A, and twice with Buffer A containing 0.1% Triton x-100. The pellets were then suspended in Laemmli sample buffer and resolved on 7.5% SDS-PAGE.

Western Immunoblotting

Nitrocellulose blots of proteins were incubated with the antibodies, and proteins were detected by enhanced chemiluminescence using horseradish peroxidase-labeled protein A, horseradish peroxidase-labeled anti rabbit IgG or horseradish peroxidase-labeled anti-mouse IgG.

PI3-kinase activation

Phosphorylation of phosphatidyl inositol was measured as follows. Cells were solubilized in Buffer C and the extracts immunoprecipitated at 4° C. with IRS-1 antibody and adsorbed onto protein A-Sepharose beads. The immunoprecipitates were washed three times with Buffer C and then washed once with Buffer B, Buffer E and Buffer F. The lipid kinase reaction was initated by addition of 100 $\mu$l sonicated phosphatidylinositol (10 $\mu$g) in kinase buffer (20 mM Hepes, pH 7.5, 10 mM $MnCl_2$ and 10 mM $MgCl_2$) containing 10 $\mu$Ci [$\gamma^{32}$P]ATP (3000 ci/m mol; Amersham). The reaction was performed at room temperature for 10 mins. and terminated by the addition of 100 $\mu$l 1 N HCl. Lipids were extracted by addition of 200 $\mu$l of a 1:1 mixture of chloroform/methanol, followed by vortexing and centrifugation at 14,000×g for 10 mins. The chloroform-containing lipid phase was then re-extracted with 150 $\mu$l of a 1:1 mixture of 1N HCl/methanol, followed by vortexing and centrifugation at 14,000×g for 10 mins. The 30 $\mu$l of the chloroform phase were resolved by thin layer chromatography using a chloroform/methanol/ammonium hydroxide (90:70:20 v/v)) running buffer. Detection of phosphorylated lipid was performed by autoradiography.

Cell Death Estimation

Subconfluent cultures of MCF-7 cells in 35 mm dishes, were deprived of serum for 20 hours and then exposed to 30 $\mu$g/ml cycloheximide in the presence or absence of increasing concentrations of fractionated ATA, crude ATA or EB. After 48 hours, the cells were detached with trypsin. The medium and the detached cells were pooled and centrifuged at 1000×g for 10 mins. Cell viability was estimated by adding an equivalent volume of trypan blue solution to an aliquot of suspended cells. Stained and unstained cells were counted on a hemocytometer ($10^3$ cells were counted for each determination).

Fractionation of ATA

ATA fractions were prepared as follows. 500 mg ATA were dissolved in 2 ml Buffer G (2M KSCN, 10 mM sodium phosphate, pH 7.2). The solution was applied to a 2×68 cm Bio Rad P-4 column (Bio Rad, Richmond, Calif.) equilibrated with Buffer G. The void volume fractions from 3 preparations were pooled and separated on a 2×68 cm gel column of Bio Rad P-10 in Buffer G. ATA polymers in the elution fractions were precipitated by adjusting the pH to 3.0–3.5, and concentrated by centrifugation at 6,000×g for 15 mins. The precipitated polymers were washed twice in 150 mM $NaCl_3$ mM HCl and lyophilized to dryness. Average Mrs of the ATA polymers were estimated by comparing their elution volumes with those of the following molecular weight standards: Blue dextran (2,000,000); cytochrome C (12,400); insulin (5,800); vitamin $B_{12}$ (1,350) and ($^3$H) ORG-2058 (345).

RESULTS

Example 1: Tyrosine Phosphorylation induced by ATA

Figure 2:
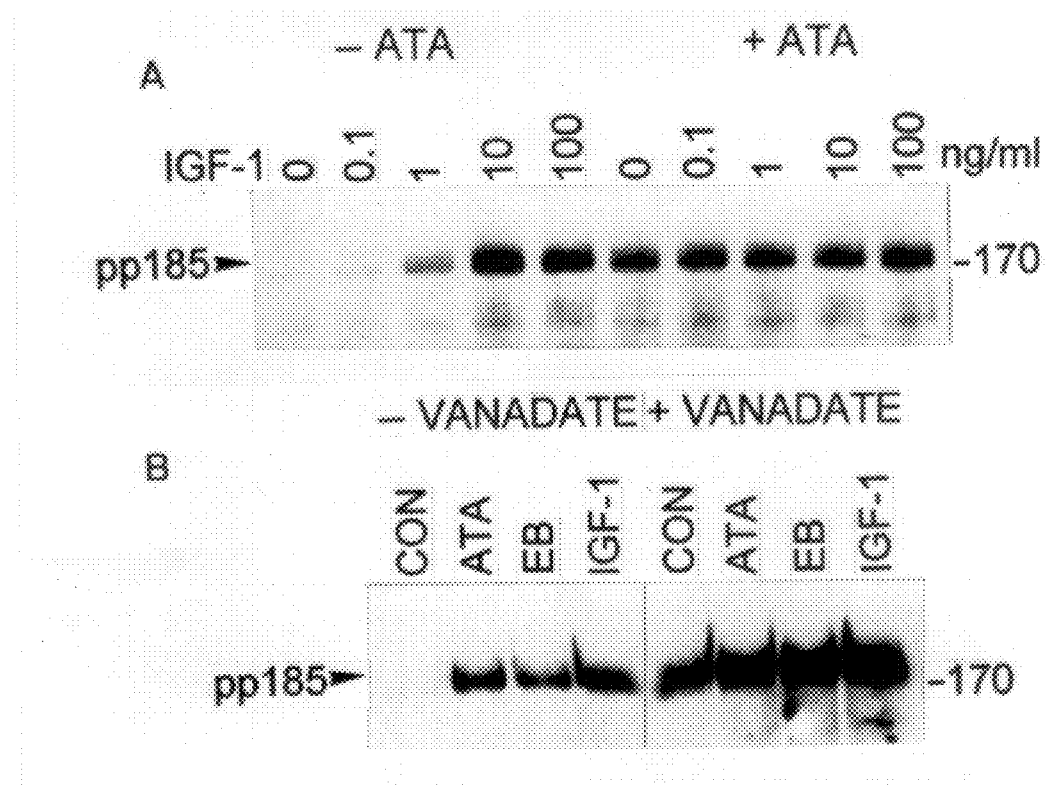
FIG. 2 is the effect of ATA and vanadate on the IGF-1 stimulated tyrosine phosphorylation of p185: A—Cells treated for 5 mins. with the indicated concentrations of IGF-1 in the presence or absence of 300 µg/ml ATA; B—Cells pre-incubated for 3 hours with or without 50 µM vanadate were incubated for 5 mins. with ATA, EB each at 300 µg/ml or with 10 ng/ml IGF-1 in the presence or absence of vanadate. Cytosols extracted in Buffer B were analyzed by immunoblotting with anti-phosphotyrosine antibody as in FIG. 1.

FIG. 1 shows tyrosine-phosphorylation of proteins in lysates of MCF-7 cells pretreated with ATA, EB, or IGF-1. As shown in FIG. 1a, the agents examined increased tyrosine phosphorylation of several proteins, but only ATA, EB and IGF-1, enhanced tyrosine phosphorylation of a 185 kDa protein(s). Both ATA and EB increased the phosphorylation of the 185 kDa protein(s) in a time and dose dependent manner (FIGS. 1b–e). Thus, phosphorylation peaked after 2 and 5 mins. exposure to ATA or EB, respectively, then decreased gradually up to 120 mins. (FIG. 1b,c). As shown in FIG. 1d,e, maximal phosphorylation in response to either ATA or EB occurs at a concentration of 300–400 μg/ml. FIG. 2 shows the effect of ATA and vanadate (a protein tyrosine phosphatase inhibitor) on IGF-1-stimulated tyrosine phosphorylation of p185. As shown in FIG. 2A IGF-1 induced phosphorylation of the 185 kDa protein(s) was unaffected by ATA. Vanadate, however, markedly enhanced the phosphorylation of p185 (FIG. 2B) induced by IGF-1 ATA and EB.

Example 2: Tyrosine Phosphorylation of IRS-1 and IRS-2 Induced by ATA and EB

Figure 3:
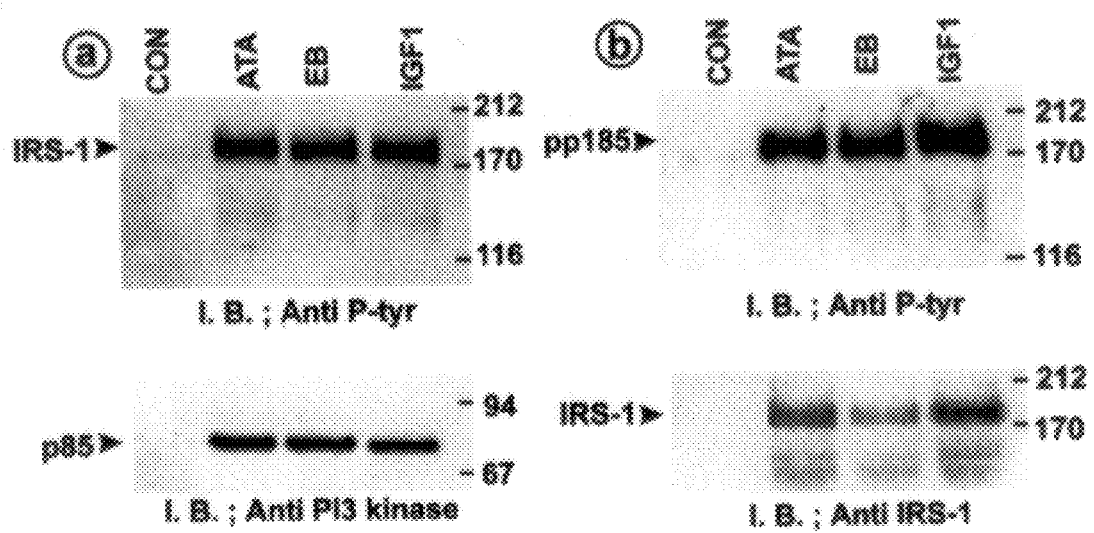
FIG. 3 is the effect of ATA and EB on tyrosine phosphorylation or IRS-1: MCF-7 cells grown in 100 mm dishes, were treated with ATA or EB, each at 300 μg/ml, or 20 ng/ml IGF-1 for 5 mins. Total cell extracts, solubilized in Buffer A, were subjected to immunoprecipitation with antibodies to IRS-1 (a) or Grb2 (b). The immunocomplexes, precipitated with protein G-Sepharose beads, were subjected to 7.5% SDS-PAGE followed by immunoblotting with a phosphotyrosine antibody, an antibody to the 85-kDa subunit of PI3-kinase or antibody to IRS-1.
Figure 4:
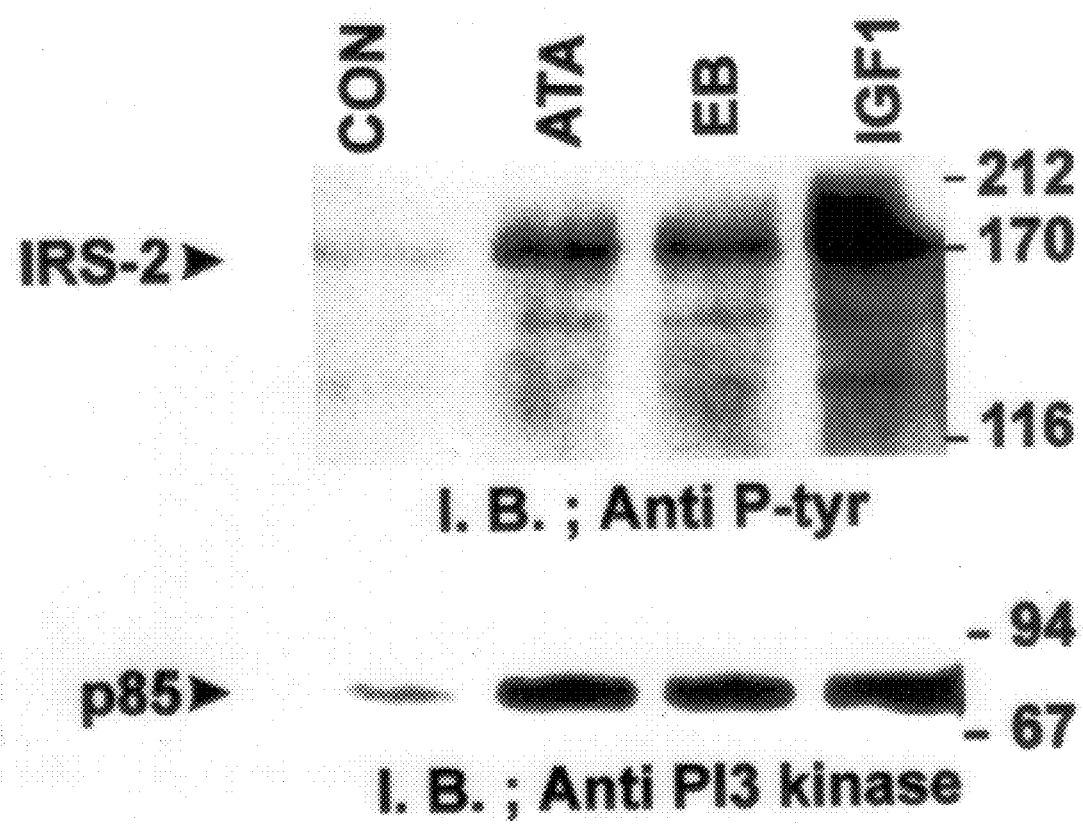
FIG. 4 is the effect of ATA and EB on tyrosine phosphorylation of IRS-2: MCF-7 cells were treated as in FIG. 3. Total cell extracts, solubilized in Buffer C, were immunoprecipitated with an antibody to IRS-2. The immunocomplexes, precipitated with protein A-Sepharose beads were subjected to 7.5% SDS-PAGE, followed by immunoblotting with a phosphotyrosine antibody and an antibody to the 85-kDA subunit of PI3-kinase.
Figure 5:
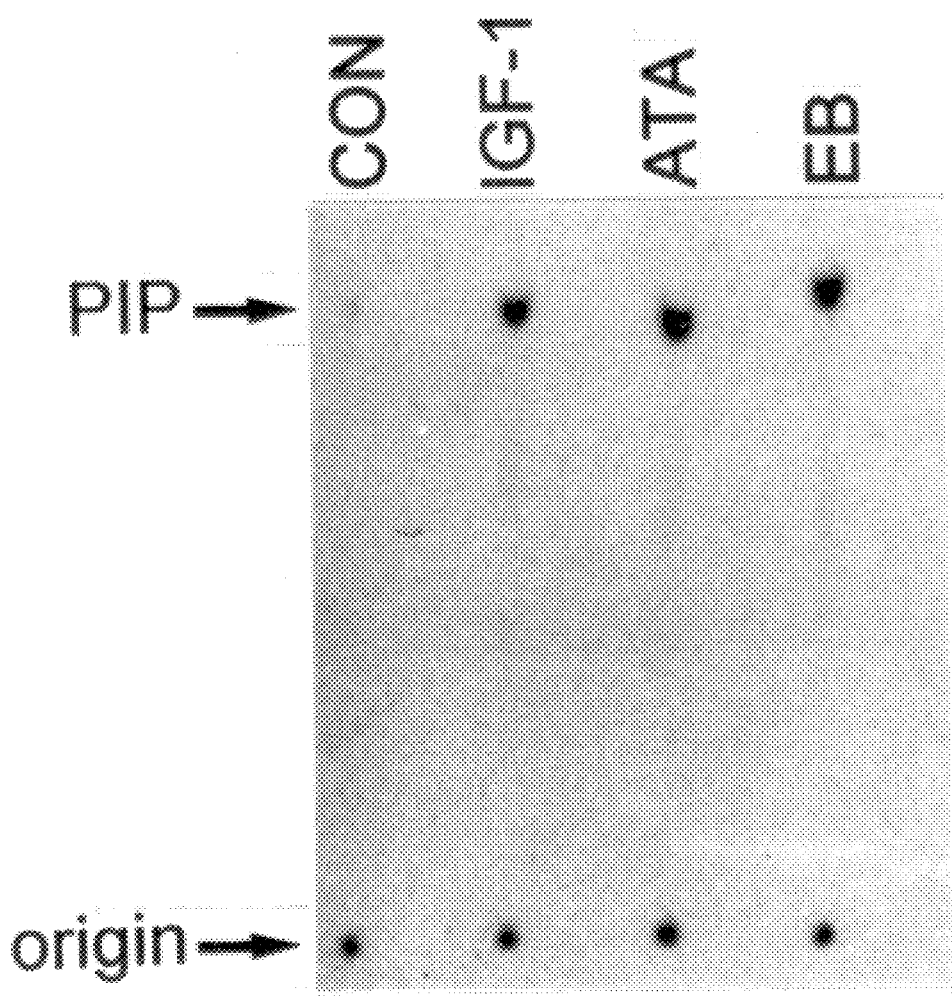
FIG. 5 is the effect of ATA and EB on the anti-IRS-1 precipitable PI3-kinase activity: Cells were treated as in FIG. 3a. Anti-IRS-1 immunoprecipitates were washed and the pellets incubated with phosphatidyl inositol and $\gamma^{32}$P-ATP. Arrows indicate the position of radioactivity corresponding to PI-3-monophosphate (PIP) and the origin.

MCF-7 cells were stimulated with ATA, EB or IGF-1, solubilized and immunoprecipitated with anti IRS-1 or IRS-2 antibodies, separated by SDS-PAGE and immunoblotted with anti-phosphotyrosine antibody. ATA, EB and IGF-1 stimulated the phosphorylation of IRS-1 (FIG. 3a, upper panel). Lysates from treated cells were immunoprecipitated with IRS-1 and IRS-2 antibody, and the immunoprecipitates were immunoblotted with an antibody to the p85 subunit of PI3-k, p85 precipitates with IRS-1 (FIG. 3a, lower panel) or IRS-2 (FIG. 4) in ATA, EB or IGF-1 treated cells. The association of IRS-1 with Grb-2 was evaluated in lysates from treated cells which were immunoblotted with antibodies to either phosphotyrosine or IRS-1. As shown in FIG. 3b, IRS-1 co-precipitated with Grb2 in ATA and EB as well as IGF-1 treated cells. As shown in FIG. 5, ATA and EB increases PI3-kinase activity similar to IGF-1.

Figure 6:
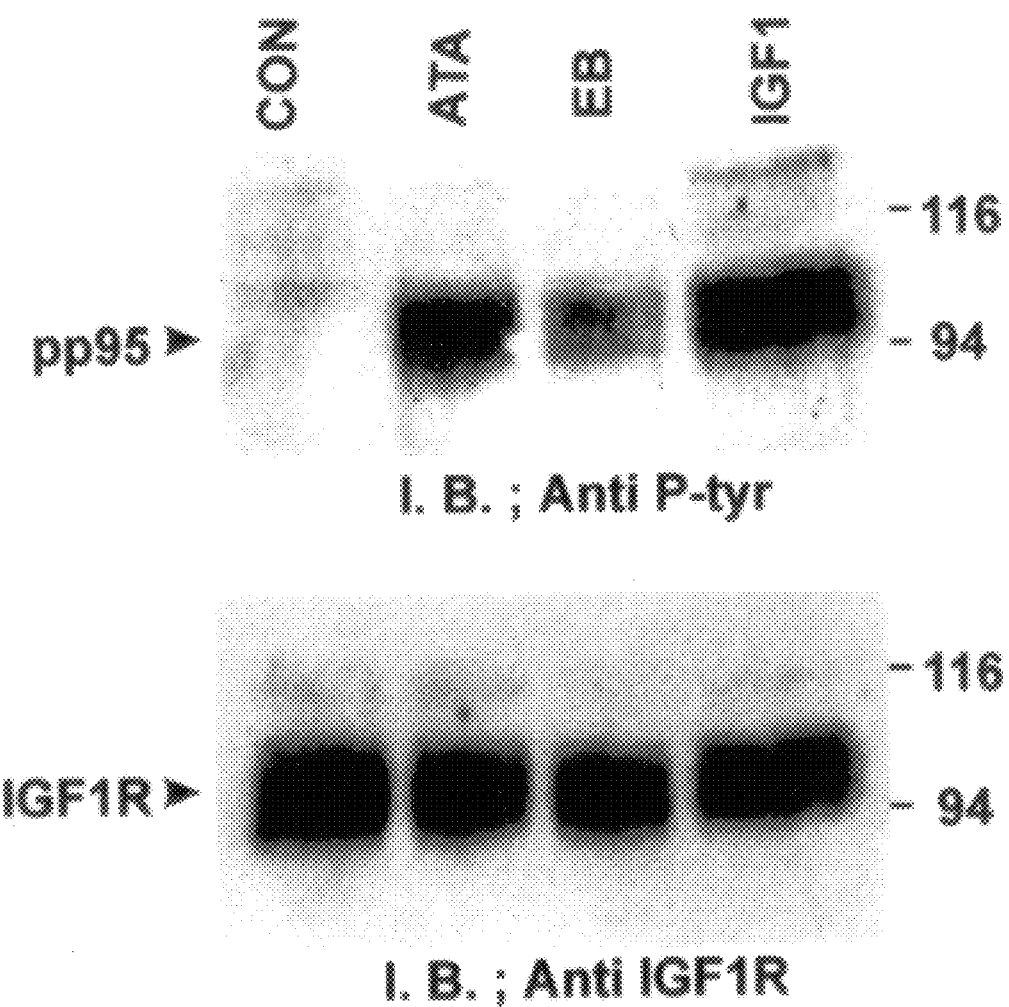
FIG. 6 is the effect of ATA and EB on tyrosine phosphorylation of IGF-1 receptor: MCF-7 cells, grown in 100 mm dishes, were treated with ATA, EB each at 300 μg/ml, or 20 ng/ml IGF-1 for 5 mins. Total cell extracts, solubilized in Buffer A, were immunoprecipitated with IGF1R antibody. The immunocomplexes precipitataed with protein G-Sepharose beads, were subjected to 7.5% SDS-PAGE followed by immunoblotting with a phosphotyrosine antibody. The membrane, after ECL detection, was stripped of bound antibody and reblotted with IGF1R antibody (IGF1R).

Example 3: Stimulation of tyrosine Phosphorylation of the IGF-1 Receptor by ATA and EB Lysates from MCF-7 cells treated with ATA, EB or IGF-1 were immunoprecipitated with anti-IGF-1 receptor antibody and the immunoprecipitates immunoblotted with an antibody to phosphotyrosine. As shown in FIG. 6, ATA and EB phosphorylated the IGF-1 receptor β subunit. Stripping and reblotting with an anti IGF-1 receptor antibody confirmed that similar amounts of the receptor were present in the immunoprecipitates.

Example 4: Activation of MAPKs

Figure 7:
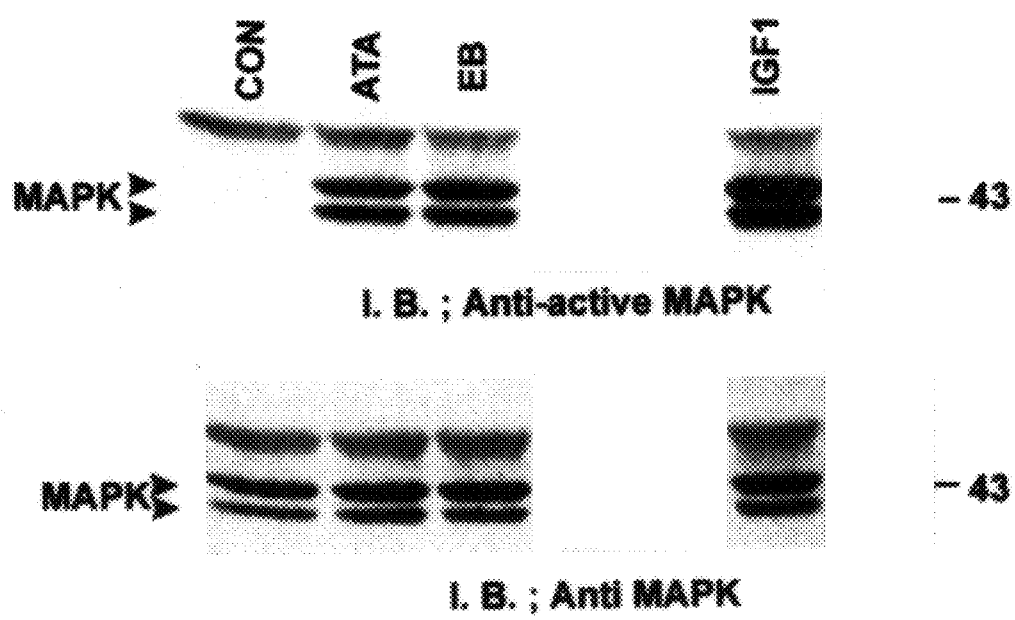
FIG. 7 is the effect of ATA and EB on activation of MAPKs: MCF-7 cells were treated for 5 mins. with ATA, EB, each at 300 μg/ml, 20 ng/ml or 40 ng/ml IGF-1. Cell lysates, solubilized in Buffer C, were subjected to 12% SDS-PAGE and immunoblotted with an anti-active MAPK antibody. The membrane, after ECL detection, was stripped of bound antibody and blotted with an anti-MAPK antibody.

The activated forms of MAPKs were detected by anti-active MAPK immunoblotting in the MCF-7 cell's lysates. As shown in FIG. 7, the two phosphorylated isoforms, MAPK-1 (44 kDa) and MAPK-2 (42 kDa) are clearly detected in blots prepared from cells treated with ATA, EB, TPA and IGF-1. Blotting with anti MAPKs antibodies confirms that similar amounts of MAPKs were present in treated and non-treated cells.

Figure 8:
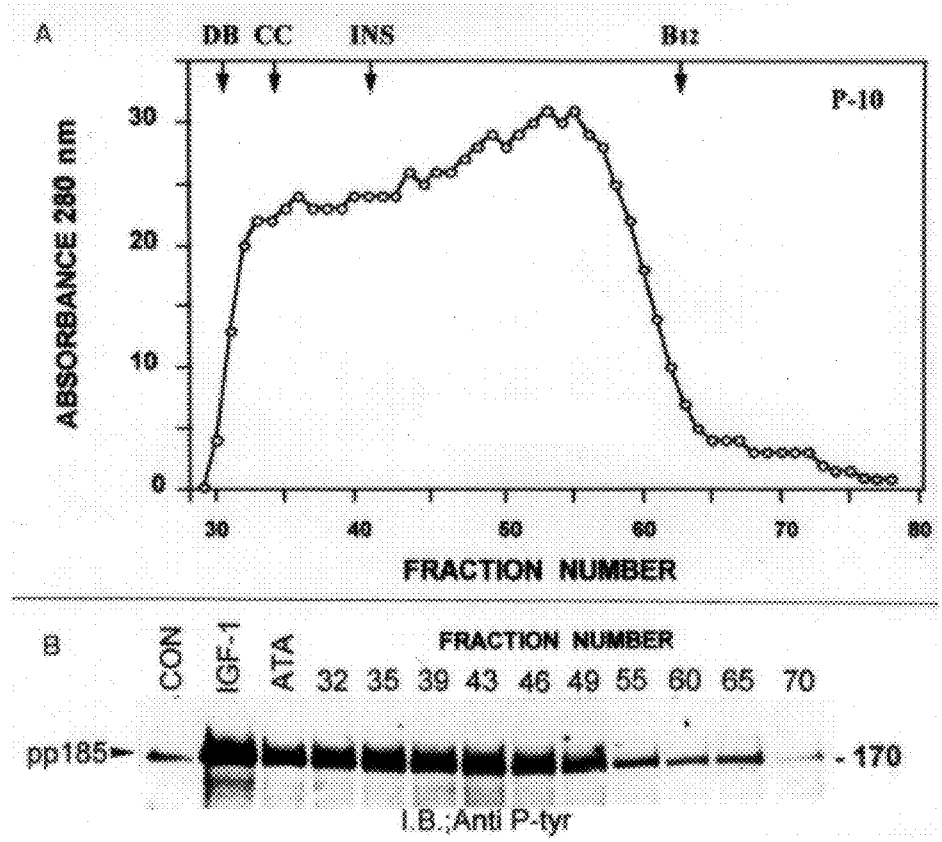
FIG. 8 is the effect of fractionated ATA on p185 phosphorylation: A—Crude ATA was separated on a Bio-Rad P-4 column and the combined void volume was then gel filtrated on a column of Bio-Rad P-10. The column was calibrated with the following molecular weight markers: DB-Dextran blue; CC-cytochrome C: Ins-insulin; B12-Vitamin B12. B—MCF-7 cells were incubated for 5 mins. with the indicated fractions of ATA (eluted from the P-10 column shown in A), crude ATA, each at 200 μg/ml or IGF-1 at 20 ng/ml. Cytosols, solubilized in Buffer B were subjected to 7.5% SDS-PAGE and immunoblotted with phosphotyrosine antibody.

Example 5: Correlation of IRS Proteins Phosphorylation and Cell Survival with Mr of Fractionated ATA ATA was fractionated into molecular weight fractions by size exclusion chromatography. Crude ATA was fractionated using a P-4 gel filtration column (Bio Rad). The void volume fractions were combined and the pooled material was further separated on a Bio Rad P-10 column (FIG. 8A). The molecular weights of the ATA polymers in the various fractions were estimated by comparing their elution volumes with those of the molecular weight standards shown. As shown in FIG. 8B and Table 1, both the survival of MCF-7 cells and the intensity of IRS-1/IRS-2 tyrosine phosphorylation increased with the Mr of the ATA polymers. Low molecular weight fractions, eluted from the P-4 column (<1300) at a concentration of 200 μg/ml did not stimulate p185 phosphorylation or inhibit cell death.

TABLE 1

Effect of fractionated ATA on p185 phosphorylation and cell survival
Subconfluent, 20 hours starved MCF-7 cells were exposed to 30 μg/ml of cycloheximide in the presence of increasing concentrations of fractionated ATA (0, 6, 12, 25, 50 μg/ml). After 48 hours, percent of dead cells was determined as described under "Experimental procedures". In the presence of cycloheximide only, 60–70% of the cells were dead after 48 hours.

| Fraction number[a] | 32 | 35 | 39 | 43 | 46 | 49 | 55 | 60 | 65 | 70 | Crude ATA | IGF-1 | Control |
|---|---|---|---|---|---|---|---|---|---|---|---|---|---|
| Average $M_r$[b] | 12,300 | 10,000 | 7,550 | 5,600 | 4,680 | 3,510 | 2,400 | 1,680 | 1,100 | >1,000 | | | |
| pp185[c] (arbitrary units) | 760 | 810 | 730 | 705 | 570 | 341 | 142 | 86 | 114 | 37 | 668 | 1,751 | 100 |
| $IC_{50}$[d] (μg/ml) | 12 | 10 | 9 | 15 | 15 | 22 | 25 | 50 | 55 | >80 | 18 | | |

[a]Fractions eluted from the P-10 column (FIG. 8A)
[b]The corresponding estimated average $M_r$.
[c]Scanned autoradiogram from FIG. 8B
[d]The concentration of fractioned ATA which inhibit 50% of cell death induced by cycloheximide.

Example 6: Phosphorylation of IR by EB and ATA

Figure 9A:
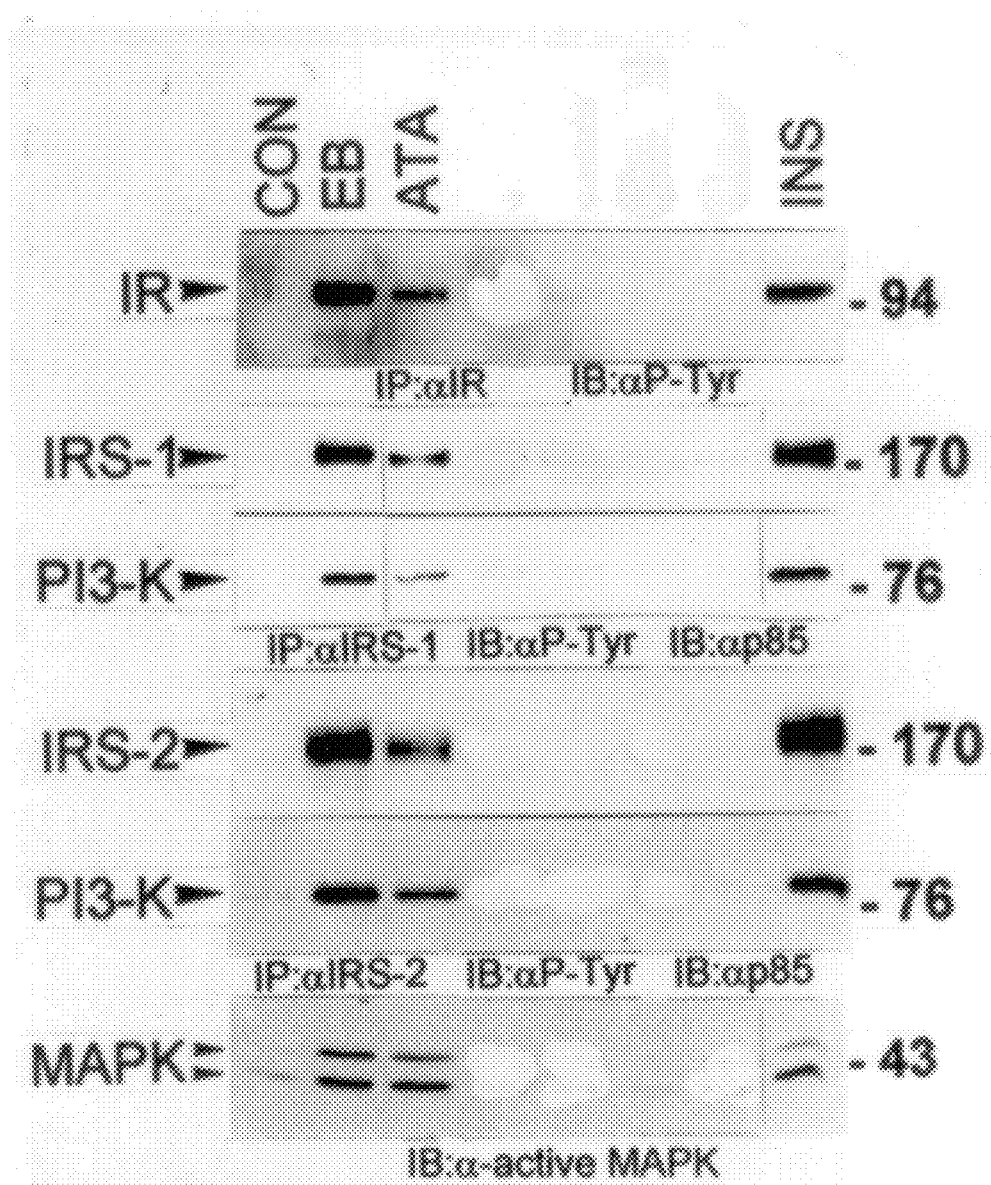
FIG. 9 is the tyrosine phosphorylation of the IR cascade in Fao cells: A—Immunoblot analysis: Fao cells were deprived of serum for 20 hours, then incubated with EB, ATA, at 200 μg/ml or insulin at 600 ng/ml for 5 mins. Cell extracts were subjected to immunoprecipitation with antibodies to: IR β-subunit (αIR), IRS-1 (αIRS-1) and to IRS-2 (αIRS-2). The immunoprecipitates and total cell extracts were analyzed by SDS-PAGE. Proteins were transferred to nitrocellulose papers, and phosphotyrosine containing proteins were probed with anti-phosphotyrosine antibodies (αP-Tyr), antibody to the 85-kDa subunit of PI3-kinase (αp85) and antibodies to active MAPK (α active MAPK). The immunoblots were visualized by ECL (Amersham).
Figure 9B:
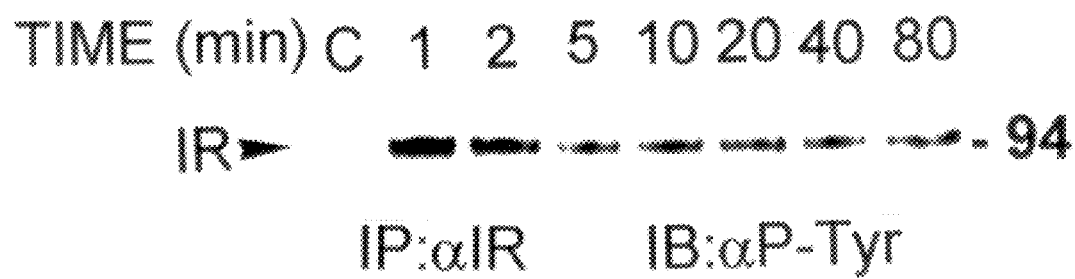

The ability of EB and ATA to phosphorylate the IR was determined in the rat hepatoma cell line FaO. EB and ATA phosphorylates IR on tyrosine residues, similar to insulin (FIG. 9A). Phosphorylation is maximal after a 1 min. exposure to 70 μg/ml of EB (FIG. 9B, top and middle panels). Inhibition of tyrosine phosphatases does not appear to be involved in the elevation of phosphorylation observed in the presence of EB since vanadate but not EB enhances the IR phosphorylation induced by insulin (FIG. 9B, bottom panel).

Figure 9C:
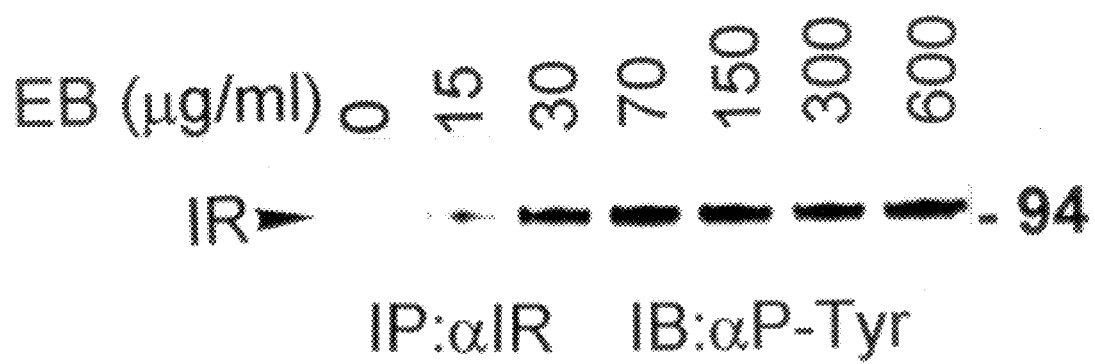
Figure 9D:
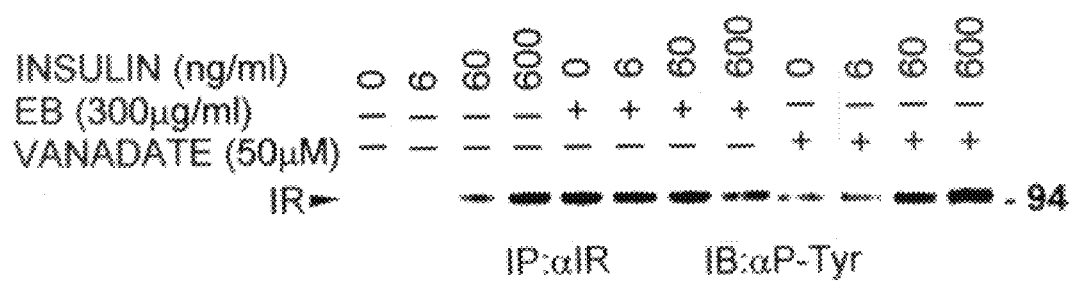
Figure 9E:
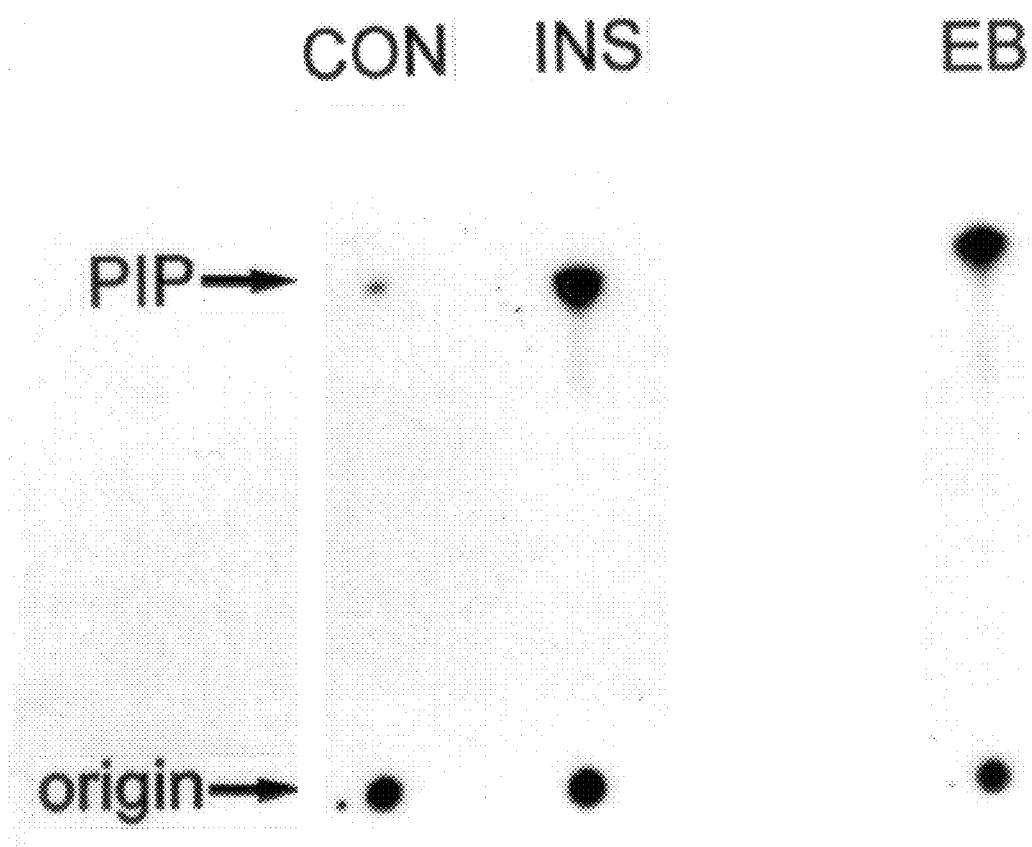

Example 7: Phosphorylation of IRS-1 and IRS-2 and their association with PI3-kinase In the rat hepatoma cell line FaO, EB and insulin, enhanced IRS-1 and IRS-2 tyrosine phosphorylation and their association with the 85-kDa regulatory subunit of the PI-kinase (FIG. 9A). PI3-kinase activity increases following its association with IRS-1 and IRS-2 (FIG. 9C). MAPKs 1 and 2 were activated by EB and insulin (FIG. 9A).

Example 8: In vivo Phosphorylation of IR

EB (20 mg/rat) or insulin (1 u/rat) was injected into about 120 g weighing Sprague-Dawley male rats, via the portal vein. Control rats were injected with saline (SAL) alone. The rats were killed and the livers excised and frozen in liquid nitrogen at the indicated times.

Figure 10A:
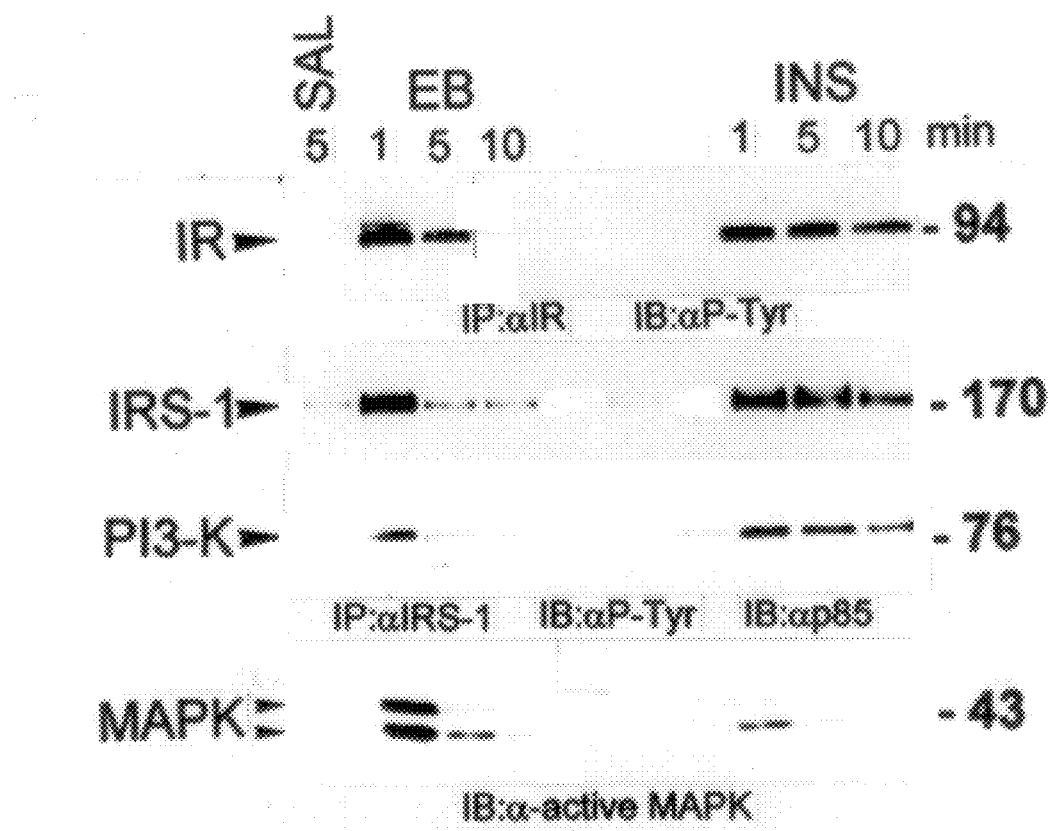
Figure 10B:
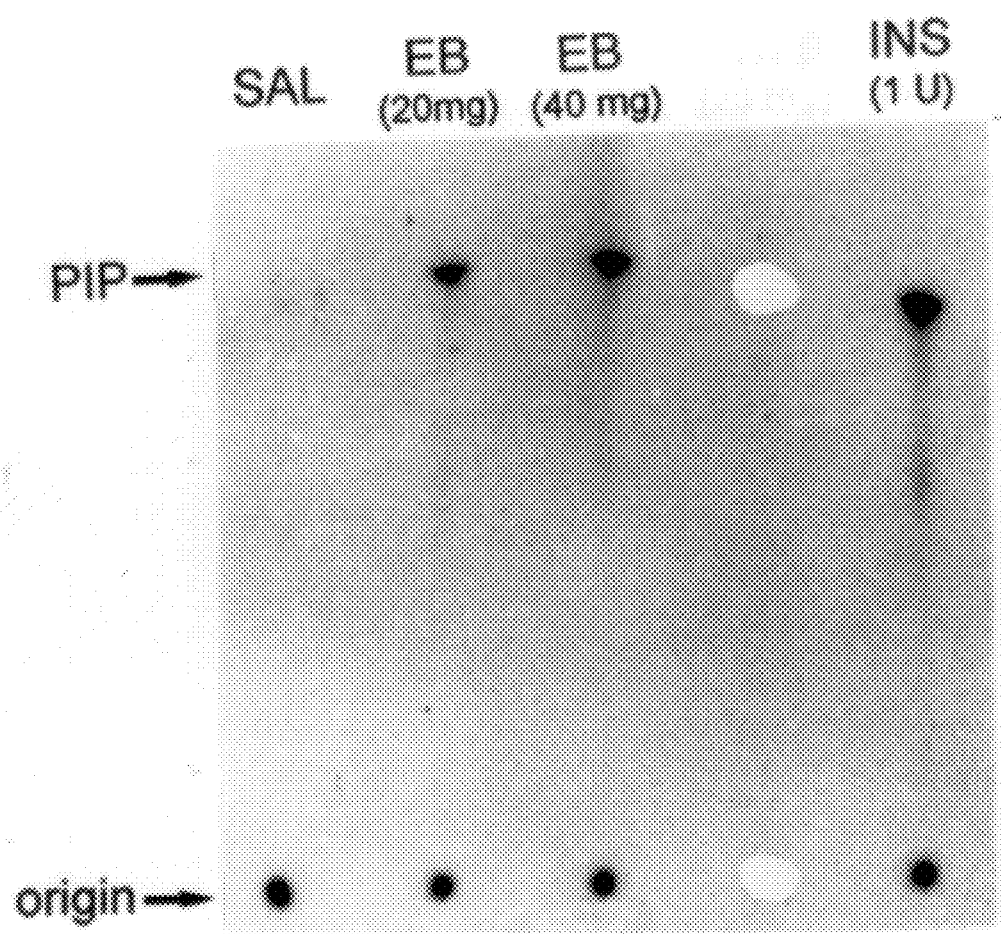

EB and insulin phosphorylated tyrosines of IR, IRS-1 and the 85-kDa of the regulatory subunit of PI3-kinase (FIG. 10A). PI3-kinase activity increased in response to EB and insulin (FIG. 10B).

Example 9: The Metabolic Effects of EB and ATA in 3T3 L1 Adipocytes

Figure 11A:
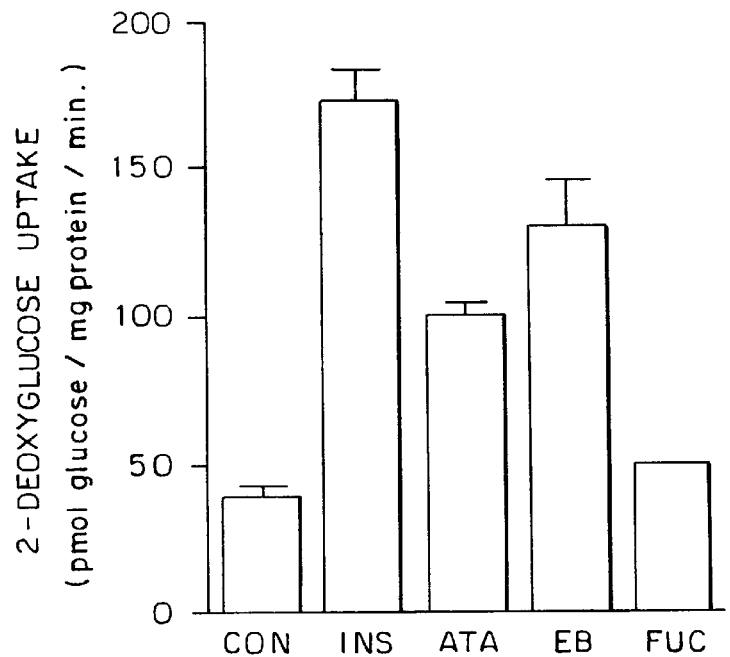
Figure 11B:
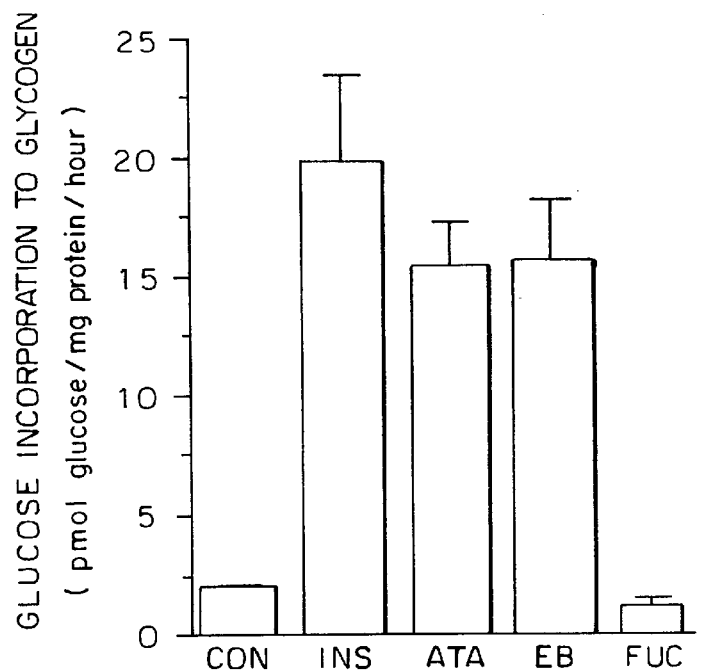
Figure 11C:
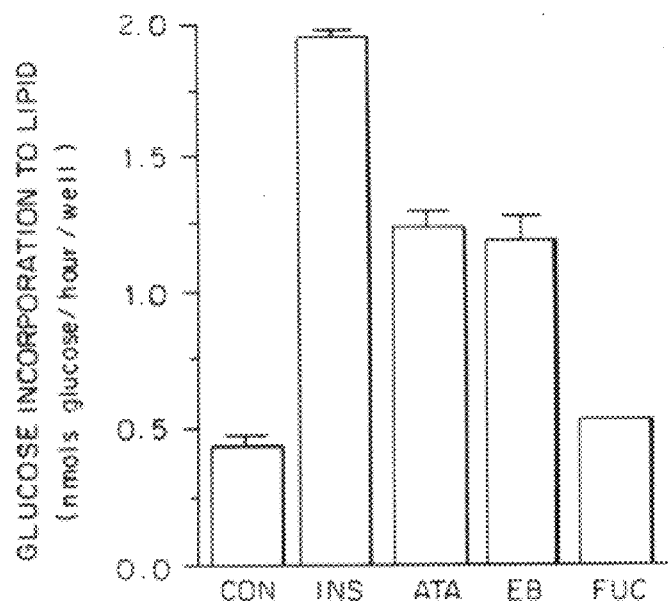
Figure 11D:
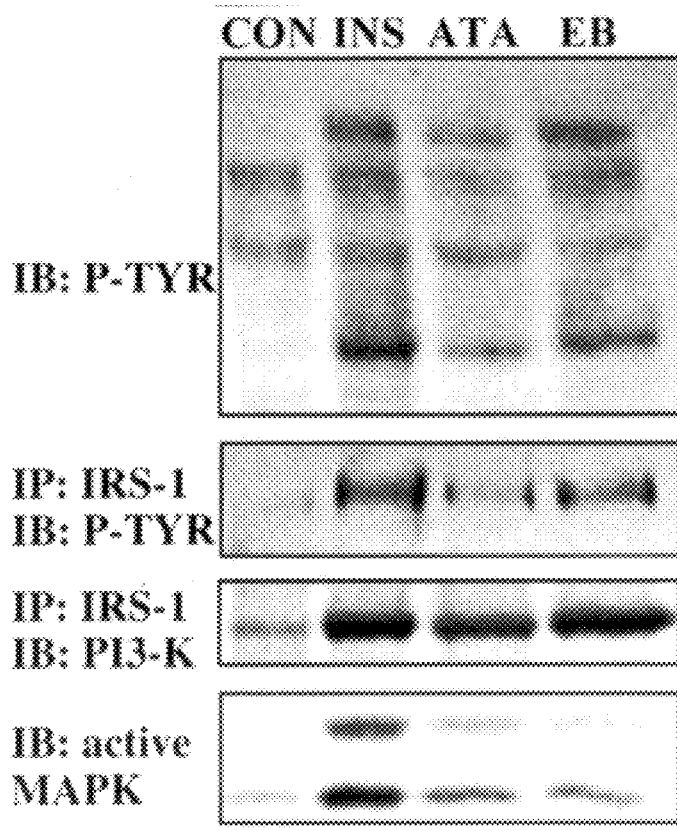

3T3 L1 adipocytes is a well known cell model for studying insulin action on glucose metabolism. EB as well as ATA and insulin, increase glucose uptake, glycogen synthesis and lipogenesis (FIG. 11). Both polyanions enhanced the tyrosine phosphorylation of IRS-1, the 85-kDa subunit of PI3-kinase, MAPK 1 and 2 and a 95-kDa protein band containing the IR as well as the IGF-1 receptor (FIG. 11D).

Example 10

Cultures of HCF-7 cells were exposed to 30 μg CX for 48 hours in the presence of EB, ATA, IGF-1, or nothing.

The percentage of dead cells in the cultures was then determined. EG and ATA reduced the percent of dead cells to that observed in cells not exposed to CX (Control) Table 2.

TABLE 2

| Agent | Percent dead cells |
|---|---|
| CX only | 56 ± 5 |
| IGF-1 (20 μg/ml) | 15 ± 4 |
| ATA (100 μg/ml) | 8 ± 3 |
| EB (380 μg/ml) | 12 ± 4 |
| Control | 10 ± 3 |

References

1. Geier et al., *J. Cell Physiol.* 163:570–576, (1995)
2. Benezra et al., *Cancer*, 52:5656–5662 (1992).
3. Miao et al., *J. Clin. Inves.*, 99:1565–1570 (1997).
4. Benezra et al., *Arteriosclerosis and Thrombosis*, 14(12): 1992–1994 (1994).
5. Regan et al., *J. Bioactive and Compatible Polymers*, 8:317–336 (1993).
6. WO 91/03226.
7. Cushman et al., *J. Med. Chem.*, 34:329–342 (1991).

We claim:

1. A method for the treatment of diabetes in a subject comprising administering to said subject in need thereof a therapeutically effective amount for diabetes treatment of a polyaromatic synthetic dye ring-containing compound which itself is active and capable of mimicking the physiological activity of insulin or insulin-like growth factor.

2. A method according to claim 1, wherein said polyaromatic ring-containing compound contains between 3 and 10 aromatic rings.

3. A method according to claim 1, wherein said polyaromatic ring-containing compound contains about 3 to about 6 aromatic rings.

4. A method according to claim 1, wherein said polyaromatic ring compound is selected from Aurintricarboxylic acid (ATA), Halogenated ATA, Sulfonated ATA, Sulfonated-Halogenated ATA, Phosphorylated ATA, Anazolene Sodium, Eosine I Bluish, Eosine Yellowish, Erythrosine, Evan's Blue (EB), Fast Green FCF, Fuchin(e) Acid, Iodophthalein Sodium, Rose Bengal, Sulfobromophthalein Sodium, Suramin Sodium, Trypan Blue, Trypan Red, Rosaniline Chloride, Crystal Violet, Methyl Blue, Methyl Green, Coomassie Blue, Basic Fuchsin, Malachite Green, Brilliant Green, Aniline blue, Brilliant Cresyl Blue, Safranin O, Ethyl Violet, Pararosaniline Acetate, Methyl Violet, Direct Yellow, Direct Red, Ponceau S, Ponceau SS, Nitrosulfonazo III, Chicago Sky Blue 6B, Calcion or RG-13577.

5. A method according to claim 4, wherein said polyaromatic ring-containing compound is Aurintricarboxylic acid.

6. A method according to claim 4, wherein said polyaromatic ring-containing compound is Evan's Blue.

7. A method according to claim 1, wherein said polyaromatic ring-containing compound further contains at least one substituent on at least two of the rings.

8. A method of claim 6, wherein the substituents are selected from $NRR_1$, $-N=R$, $-OR$, $=O$, $-NO_2$, $-COOR$, halogen, $-SO_2OR$, $-SO_2NHR$, $-OSO_2OR$ and R, wherein R is C1–C12 alkyl or hydrogen and $R_1$ is lower alkyl, hydrogen, phenyl or substituted phenyl.

9. A method according to claim 1, wherein said polyaromatic ring-containing compound is a straight or branched polymer comprising monomeric subunits selected from Aurintricarboxylic acid (ATA), Halogenated ATA, Sulfonated ATA, Sulfonated-Halogenated ATA, Anazolene Sodium, Eosine I Bluish, Eosine Yellowish, Erythrosine, Evan's Blue, Fast Green FCF, Fuchin(e) Acid, Iodophthalein Sodium, Rose Bengal, Sulfobromophthalein Sodium, Suramin Sodium, Trypan Blue, Trypan Red, Rosaniline Chloride, Crystal Violet, Methyl Blue, Methyl Green, Coomassie Blue, Basic Fuchsin, Malachite Green, Brilliant Green, Aniline blue, Brilliant Cresyl Blue, Safranin O, Ethyl Violet, Pararosaniline Acetate, Methyl Violet, Direct Yellow, Direct Red, Ponceau S, Ponceau SS, Nitrosulfonazo III, Chicago Sky Blue 6B, Calcion, or RG-13577.

10. A method according to claim 9, wherein said polyaromatic ring-containing compound is a straight or branched polymer of Aurintricarboxylic acid.

11. A method according to claim 10, wherein the molecular weight of the straight or branched polymer of aurintricarboxylic is at least 1,300.

12. A method according to claim 1, wherein said polyaromatic ring-containing compound is administered in the presence of a pharmaceutically acceptable carrier.

13. A method according to claim 1, wherein said administration is by oral route.

14. A method for the treatment of a disorder in a subject, said disorder being selected from:

a. diabetes, b. cardiomyopathy, c. growth hormone deficiency or resistance, d. osteoporosis, e. impaired cognition, f. inappropriate apoptosis, g. aging, or h. impaired muscle formation, said method comprising the administration to a human or an animal in need of such treatment an amount effective for said treatment of a polyaromatic synthetic dye ring-containing compound which itself is active and capable of mimicking the physiological activity of insulin or insulin-like growth factor.

15. A method according to claim 14, wherein said polyaromatic ring-containing compound is administered in the presence of a pharmaceutically acceptable carrier.

16. A method according to claim 14, wherein said administration is by oral route.

* * * * *